lUS008361055B2

(12) United States Patent  (10) Patent No.: US 8,361,055 B2
Tucker  (45) Date of Patent: Jan. 29, 2013

(54) SYRINGE AND METHOD FOR RECONSTITUTION OF DRY-FORM DRUGS AND MEDICINES

(76) Inventor: Peter L. Tucker, Charlotte, NC (US)

(*) Notice: Subject to any disclaimer, the term of this patent is extended or adjusted under 35 U.S.C. 154(b) by 456 days.

(21) Appl. No.: 12/626,393

(22) Filed: Nov. 25, 2009

(65) Prior Publication Data
US 2010/0130961 A1  May 27, 2010

Related U.S. Application Data

(60) Provisional application No. 61/117,815, filed on Nov. 25, 2008.

(51) Int. Cl.
*A61M 31/00* (2006.01)
(52) U.S. Cl. .................. 604/518; 604/82; 604/416
(58) Field of Classification Search .............. 604/416, 604/518–520, 82, 92
See application file for complete search history.

(56) References Cited

U.S. PATENT DOCUMENTS 7,128,105 B2 * 10/2006 Tribble et al. ................. 141/319

* cited by examiner

*Primary Examiner* — Kevin C Sirmons
*Assistant Examiner* — Deanna K Hall
(74) *Attorney, Agent, or Firm* — Tillman Wright, PLLC; James D. Wright; Chad D. Tillman

(57) ABSTRACT

A method of reconstituting and administering an injectable fluid distributed to practitioners in dry-form includes receiving a drug or medicine in dry form, selecting a reconstitution concentration for the drug or medicine, reconstituting a desired number of units of the drug or medicine by adding diluent to the dry-form drug or medicine, selecting a syringe having units marked according to the selected reconstitution concentration, drawing up a desired number of drug or medicine units using the selected syringe, and administering a desired number of units according to the unit markings on the selected syringe. Such a syringe includes a barrel, a plunger assembly that has a plunger handle and a piston, a needle, and a needle cap. The syringe includes a visual indicia, representing a first drug concentration contained in the barrel, that is distinguishable from a corresponding visual indicia, on a second syringe, representing a second drug concentration.

17 Claims, 8 Drawing Sheets

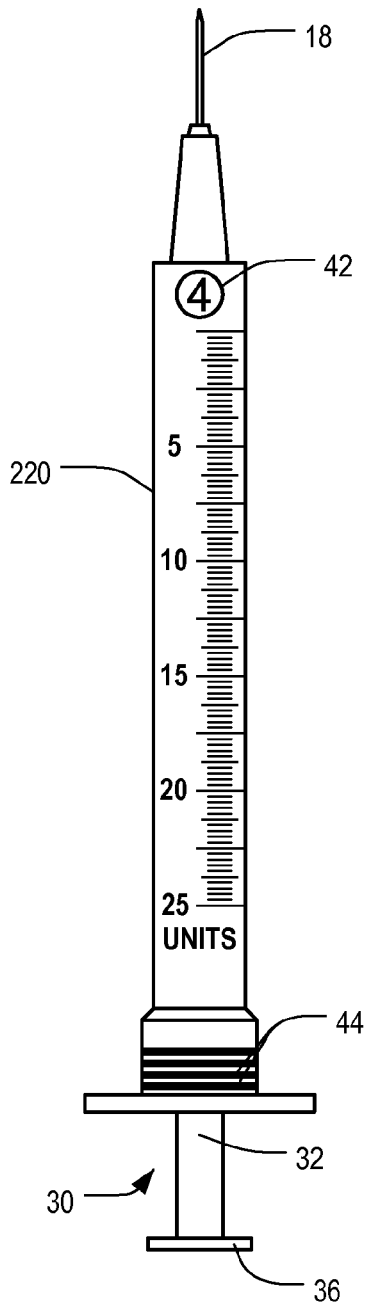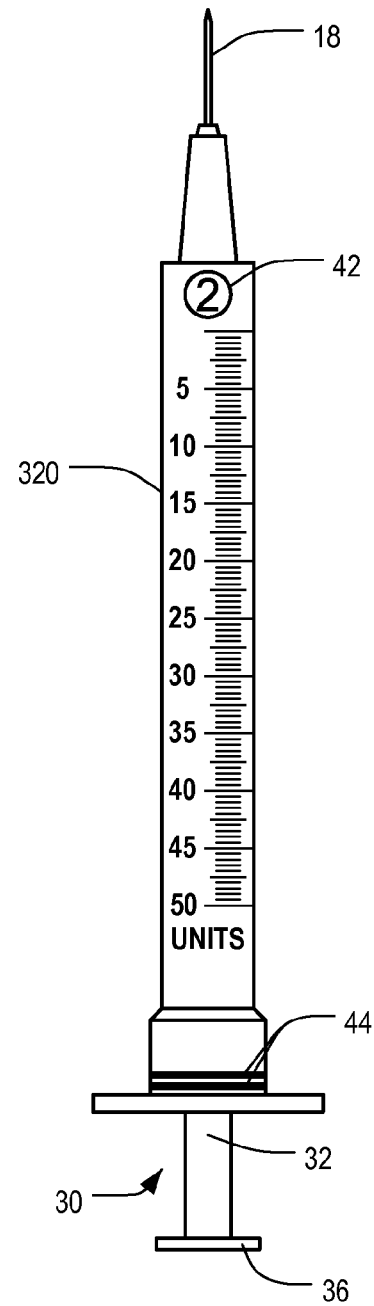
FIG. 5A  FIG. 5B

SYRINGE AND METHOD FOR RECONSTITUTION OF DRY-FORM DRUGS AND MEDICINES

CROSS-REFERENCE TO RELATED APPLICATIONS

The present application is a U.S. nonprovisional patent application of, and claims priority under 35 U.S.C. §119(e) to, U.S. Provisional Patent Application No. 61/117,815, filed Nov. 25, 2008 and titled "SYRINGE AND METHOD FOR RECONSTITUTION OF DRY-FORM DRUGS AND MEDICINES." The entire disclosure of such application is incorporated herein by reference.

COPYRIGHT STATEMENT

All of the material in this patent document is subject to copyright protection under the copyright laws of the United States and of other countries. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE PRESENT INVENTION

1. Field of the Present Invention

The present invention relates generally to the field of syringes, and in particular, to syringes for use with reconstituted drugs and medicines.

2. Background

Syringes are very well known for use in administering drugs, medicines and the like in fluid (liquid or gaseous) form. A syringe is generally a simple piston pump having a plunger that fits tightly in a tube or barrel. By first pulling the plunger from one end of the barrel, a drug, medicine in liquid or gaseous form may be drawn into the barrel through an orifice at the opposite end. The plunger may then be pushed back into the barrel, causing the medicine to be expelled through the orifice. By fitting the orifice end with a hypodermic needle, the medicine may be injected into body tissues.

Dosages of such injectable fluids, such as lidocaine, are commonly measured in milliliters (mL) or cubic centimeters (cc). FIG. 1 is a side view of a conventional syringe, marked in units of milliliters. A dosage of 1.0 mL may be measured by drawing enough of the liquid material up into the syringe such that the liquid passes the 1.0 mL marking on the barrel of the syringe. Conventionally, the syringe is held upside down, tapped to shake air bubbles to the top, and then expelling a small amount of the medicine to bring the level down to exactly 1.0 mL. The syringe is then ready for use. More particularly, if the syringe is a hypodermic syringe and the liquid is to be injected into a body tissue, the syringe is ready for such injection.

For reconstituted drugs, it is well established that different dosages may utilize different concentrations of the medicine, drug or the like being administered. For example, a particular drug could be given in a dose of 1.0 mL, or could be diluted with 1.0 mL of saline, in which case the drug amount would remain the same but the total amount of liquid being administered would be 2.0 mL.

However, there are some drugs for which it may be preferable to distribute the drug in a standardized concentration. This may be for convenience, safety, or any of a variety of other reasons. For example, in the United States, insulin is conventionally provided only in a concentration of 100 U/mL. In conjunction with this, insulin is provided in special syringes that are marked in "units" rather than in mL. In particular, insulin is often provided in syringes containing 50 or 100 standard units and marked in single unit increments. By using such a standardized approach, insulin can be manufactured, distributed and used in only a single standard concentration, with the end user being able to measure the proper dosage accurately without need for mathematical conversions or the like, thus making the administration of insulin safer and more convenient.

Variable concentration levels may be utilized with regard to drugs and medicines that are distributed by the manufacturer in dry form (typically in the form of a vacuum-dried powder) and reconstituted by a medical practitioner or staff member. Some such drugs and medicines, such as botulinum toxin type A (sold for example under the trade names BOTOX®, DYSPORT®, Reloxin™ and Puretox™) and botulinum toxin type B (sold for example under the trade name Myobloc®), may be reconstituted from dry form of the drug to a variety of dilution or concentration levels.

In some such drugs and medicines, however, there are various acceptable concentration (dilution) levels, some of which may be established by policy, by individual diagnosis, by personal preference, or the like. In practice, for example, BOTOX® (sometimes referred to herein as "Botox") may be sold in various numbers of units per milliliter. Unfortunately, traditional syringes used in conjunction with reconstituted Botox, as well as with various other injectable fluids that are reconstituted by practitioners from their dry form, provide only an indication of fluid volume, and not the drug or medicine units contained therein.

The situation is further complicated by the fact that different manufacturers sometimes use different standard units to measure otherwise comparable versions of some drugs and medicines. For example, although very similar, Botox is commonly provided by the manufacturer in 100-unit packages or increments, while DYSPORT® (sometimes referred to herein as "Dysport") is commonly provided by the manufacturer in 300-unit packages or increments, and the relative units are not necessarily equivalent.

Thus, a need still exists for apparatuses and methods for proper reconstitution and subsequent handling and administering of injectable fluids distributed to practitioners in dry-form.

SUMMARY OF THE PRESENT INVENTION

Broadly defined, the present invention according to one embodiment is a method of reconstituting and administering an injectable fluid distributed to practitioners in dry-form, including: receiving a drug or medicine in dry form; selecting a reconstitution concentration for the drug or medicine; reconstituting a desired number of units of the drug or medicine by adding diluent to the dry-form drug or medicine; selecting a syringe having units marked according to the selected reconstitution concentration; drawing up a desired number of drug or medicine units using the selected syringe; and administering a desired number of units according to the unit markings on the selected syringe.

A method of reconstituting and administering an injectable drug or medicine, distributed to practitioners in dry form, including: receiving a drug or medicine in dry form; selecting a reconstitution concentration for the drug or medicine; reconstituting a desired number of units of the drug or medicine by adding diluent to the dry-form drug or medicine; selecting a syringe marked in correspondence to the selected reconstitution concentration; drawing up a desired number of drug or medicine units using the selected syringe; and administering a desired number of units according to the unit markings on the selected syringe. In a feature of this aspect, the step of selecting a reconstitution concentration includes selecting the reconstitution concentration from a plurality of different standardized reconstitution concentrations. In a further feature, the step of selecting a syringe includes selecting the syringe from a plurality of differently-marked syringes, wherein the markings on each of the plurality of syringes is representative of a particular standardized reconstitution concentration of the plurality of different standardized reconstitution concentrations.

In a further feature, the selected syringe is marked with units according to the selected reconstitution concentration, thereby indicating to a user the number of units of the drug contained in the syringe.

In a still further feature, the selected syringe is marked with an alphanumeric character indicating, to a user, the selected reconstitution concentration. In further features, the alphanumeric character includes a number representative of the number of mL of diluent to be added to a predetermined quantity of the dry-form drug, thereby reconstituting the drug (and, optionally, the predetermined quantity of the dry-form drug is 100 units or 300 units); the alphanumeric character includes a letter; and/or the alphanumeric character includes a code representative of the selected reconstitution concentration.

In a still further feature, the selected syringe is marked with a non-alphanumeric code that is representative of the selected reconstitution concentration. In further features, the non-alphanumeric code includes one or more rings wherein the number of rings is indicative of the selected reconstitution concentration; and/or the non-alphanumeric code includes a color code wherein the color of one or more elements of the syringe are indicative of the selected reconstitution concentration.

In a still further feature, the reconstituting step includes reconstituting the desired number of units of the drug or medicine by adding the diluent to the dry-form drug or medicine at the selected reconstitution concentration.

In a still further feature, the selected syringe is marked with a manufacturing source identifier, thereby indirectly providing an indication of the unit measure, of a plurality of possible unit measures, with which the selected syringe is to be used.

In a still further feature, the selected syringe is marked with an indication of the unit measure, of a plurality of possible unit measures, with which the selected syringe is to be used.

Broadly defined, the present invention according to another embodiment is a syringe for use with reconstitution and administration of an injectable drug, distributed to practitioners in dry-form, including: a barrel; a plunger assembly, including a plunger handle and a piston; a needle; and a needle cap; wherein at least one of the barrel, plunger assembly and needle cap include a visual indicia, representative of a first concentration of a drug in a reconstituted injectable fluid contained in the barrel, that is distinguishable from a corresponding visual indicia, on a second syringe, that is representative of a second concentration of a drug in a reconstituted injectable fluid contained in the second syringe.

In a feature of this aspect, each visual indicia is in the form of a number, such that the particular number indicates the respective concentration.

In another feature of this aspect, each visual indicia is in the form of one or more rings, such that the particular number of rings indicates the respective concentration.

In another feature of this aspect, each visual indicia is in the form of a color, such that the particular color indicates the respective concentration.

In another feature of this aspect, each of the barrel, plunger assembly and needle includes the visual indicia.

In another feature of this aspect, the syringe is marked with a manufacturing source identifier, thereby indirectly providing an indication of the unit measure, of a plurality of possible unit measures, with which the syringe is to be used.

In another feature of this aspect, the syringe is marked with an indication of the unit measure, of a plurality of possible unit measure, with which the syringe is to be used.

Broadly defined, the present invention according to another embodiment is a method of distributing an injectable drug or medicine, provided in dry form, for reconstitution and administration, including: packaging an injectable drug or medicine, in dry form, for distribution; procuring a supply of syringes for use with a reconstituted form of the dry-form injectable drug or medicine, wherein each syringe is marked in such a way as to indicate, to a user, the concentration of the drug or medicine to be contained in the syringe when reconstituted and drawn thereinto, and wherein the supply of syringes include a multitude of each of a plurality of differently-marked syringes such that different syringes are to be used with different reconstitution concentrations; and providing a quantity of the injectable drug or medicine to a practitioner in conjunction with one or more syringe together with printed information instructing a user with regard to the reconstitution of the drug or medicine in the concentration corresponding to the marking on the one or more syringe.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

Further features, embodiments, and advantages of the present invention will become apparent from the following detailed description with reference to the drawings, wherein:

FIGS. 5A and 5B are side views of hypodermic syringes similar to that of FIG. 2 but with markings indicating the concentration of the drug that is to be drawn into the respective syringe;

DETAILED DESCRIPTION OF THE PREFERRED EMBODIMENTS

Figure 1:
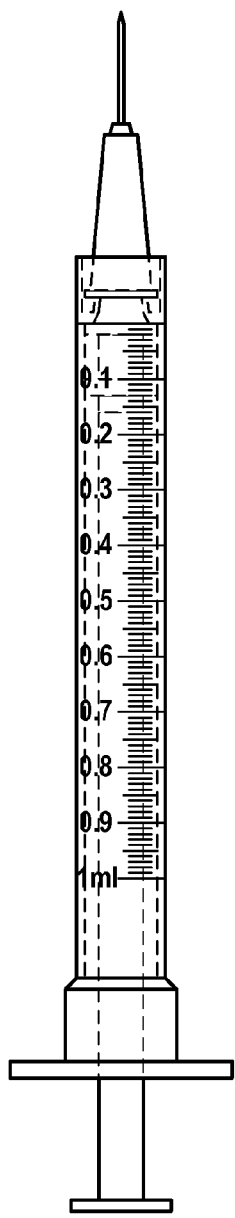
FIG. 1 is a side view of a conventional syringe, marked in units of milliliters.

As a preliminary matter, it will readily be understood by one having ordinary skill in the relevant art ("Ordinary Artisan") that the present invention has broad utility and application. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, in which like numerals represent like components throughout the several views, the preferred embodiments of the present invention are next described. The following description of the preferred embodiment(s) is merely exemplary in nature and is in no way intended to limit the invention, its application, or uses.

Figure 2:
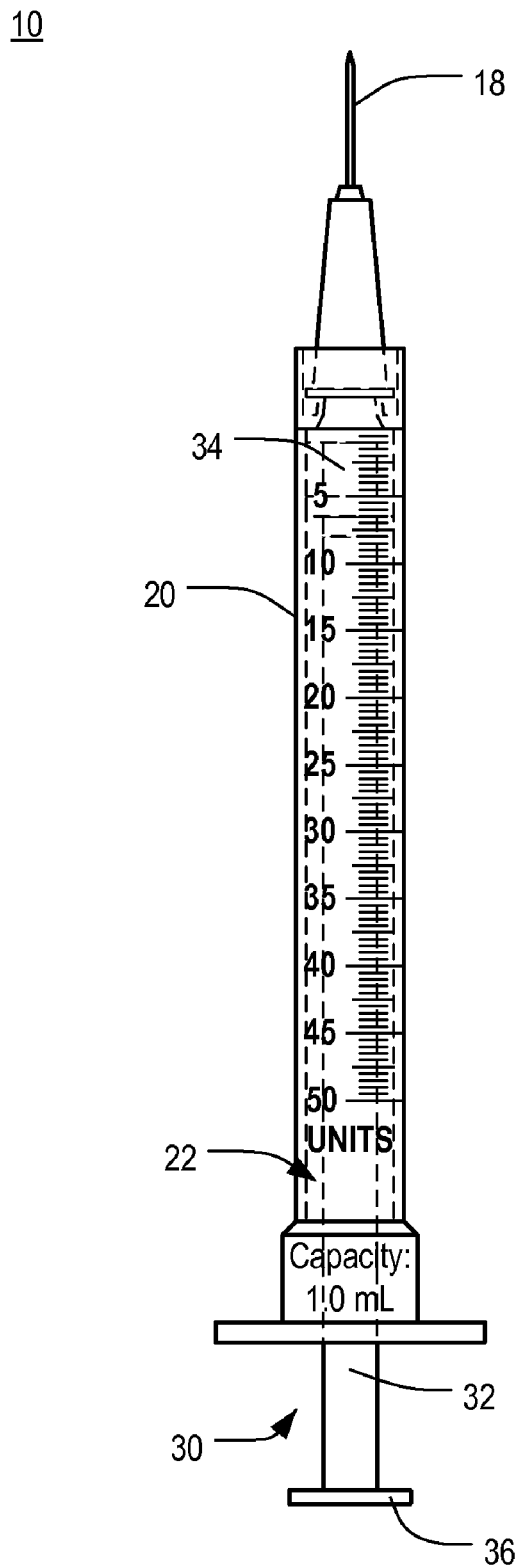
FIG. 2 is a side view of a hypodermic syringe marked with dosage unit increments in accordance with one or more preferred embodiments of the present invention.
Figure 3:
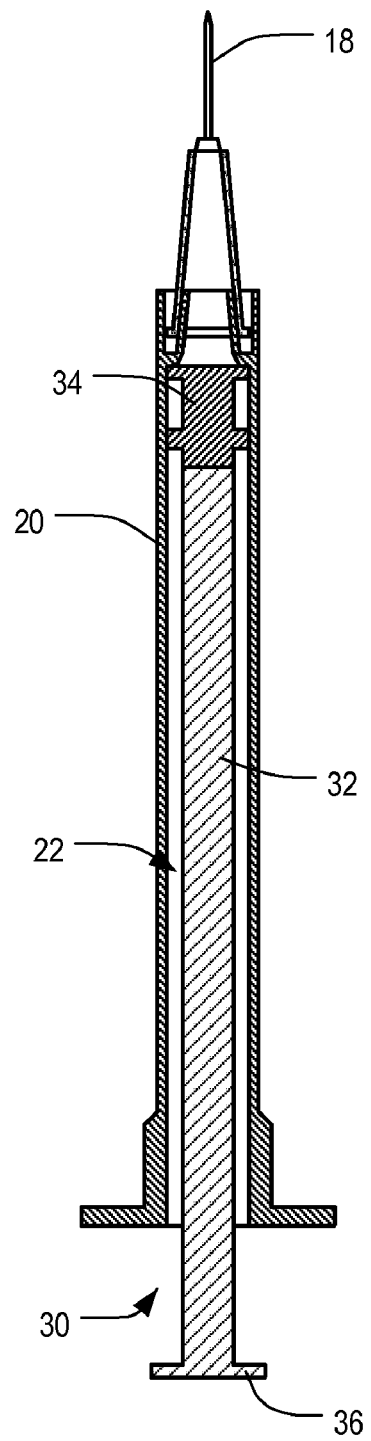
FIG. 3 is a side cross-sectional view of the syringe of FIG. 2.

FIGS. 2 and 3 are a side view and a side cross-sectional view of a hypodermic syringe 10 in accordance with one or more preferred embodiments of the present invention. It will be appreciated that, for the sake of clarity, the syringe 10 of FIG. 2 is shown as being at least partially transparent, wherein broken lines are used to indicate interior surfaces. With reference to both FIGS. 2 and 3, the syringe 10 may be constructed generally conventionally, with a barrel 20, a plunger assembly 30 and a hollow needle 18. The barrel 20 defines an interior cylinder 22 within which the plunger assembly 30 is fitted. The plunger assembly 30 includes a piston 32, a rubber gasket 34 and a handle 36 extending from one end of the barrel 20. The hollow needle 18 is coupled, preferably removably such as via a hand-tightened threaded fitting such as a Luer lock, to the opposite end of the barrel 20, and the interior of the needle 18 is in fluid communication with the interior of the barrel 20. As a safety precaution, the needle 18 is typically covered with a removable cap (not shown) when not in use.

Figure 4:
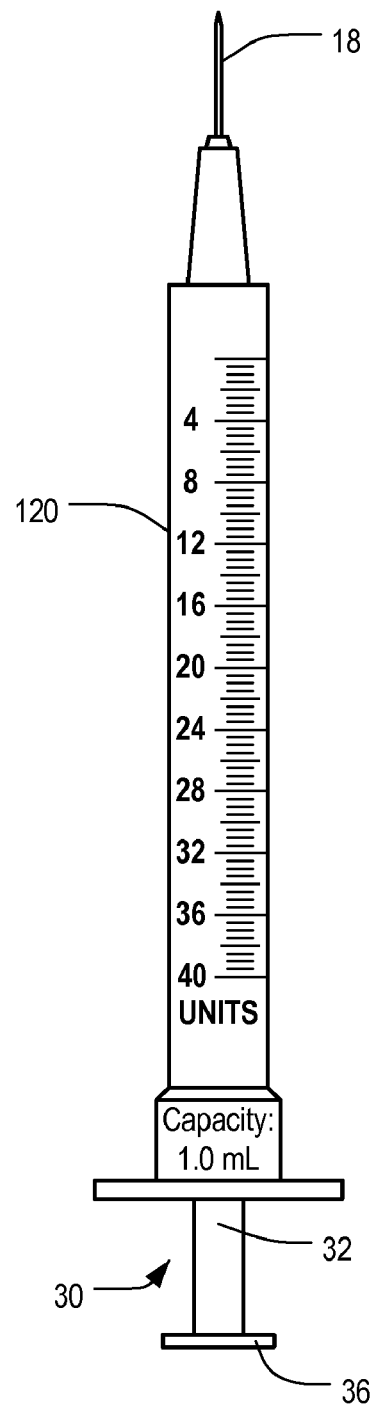
FIG. 4 is a side view of a hypodermic syringe similar to that of FIG. 2 but marked in different dosage unit increments.

Notably, the barrel 20 of the syringe 10 of FIGS. 2 and 3 is marked in increments of dosage units rather than in hundredths of mL, as in the conventional syringe of FIG. 1. In particular, as shown in FIG. 2, the barrel 20 has increments totaling 50 units. If the syringe 10 is a 1 mL syringe (i.e., of the same volume as the syringe of FIG. 1), then the syringe 10 shown in FIG. 2 is to be understood to have, and should preferably only be used with, a dosage concentration of 50 units ("U")/1 mL. FIG. 4, on the other hand, is a side view of a hypodermic syringe 110 that is generally similar to that of FIG. 2 but is marked in different dosage unit increments. In particular, the barrel 120 has increments totaling 40 units. If the syringe 110 is a 1 mL syringe (i.e., of the same volume as the syringe of FIG. 1 and as the syringe 10 of FIG. 2), then the syringe 110 shown in FIG. 4 is to be understood to have, and should preferably only be used with, a dosage concentration of 40 units ("U")/1 mL.

The barrel 20 may also be marked to indicate the concentration level of the solution in the syringe 10, i.e, the amount of diluent that is used to reconstitute the drug. The capacity may be marked by printing a number 42, a code 44 (such as a number of rings), or the like, representative of the concentration (in U/mL) of the syringe 10, on the barrel 20 thereof. For example, the number 42, code 44, or the like may directly indicate the amount of diluent used to reconstitute 100 units of the drug.

In one such implementation, a "#1" syringe (marked "1" and/or having one ring around the barrel) may indicate that the drug in the syringe has been reconstituted or diluted at a concentration of 1 mL of saline for every 100 units of the drug, a "#2" syringe (marked "2" and/or having two rings around the barrel) may indicate that the drug in the syringe has been reconstituted or diluted at a concentration of 2 mL of saline for every 100 units of the drug, a "#3" syringe (marked "3" and/or having three rings around the barrel) may indicate that the drug in the syringe has been reconstituted or diluted at a concentration of 3 mL of saline for every 100 units of the drug, a "#4" syringe (marked "4" and/or having four rings around the barrel) may indicate that the drug in the syringe has been reconstituted or diluted at a concentration of 4 mL of saline for every 100 units of the drug, and a "#5" syringe (marked "5" and/or having five rings around the barrel) may indicate that the drug in the syringe has been reconstituted or diluted at a concentration of 5 mL of saline for every 100 units of the drug. In this example, it will be appreciated that a #1 1 mL syringe, if fully drawn up, would thus contain 100 units of the drug, a #2 1 mL syringe, if fully drawn up, would thus contain 50 units of the drug, a #3 1 mL syringe, if fully drawn up, would thus contain 33 units of the drug, a #4 1 mL syringe, if fully drawn up, would thus contain 25 units of the drug, and a #5 1 mL syringe, if fully drawn up, would thus contain 20 units of the drug. Two such syringes are illustrated in FIGS. 5A and 5B, wherein the syringe 210 in FIG. 5A has a "4" printed near one end of the barrel 220 and 4 rings printed near the opposite end of the barrel 220 and thus contains a concentration of 4 mL of diluent per 100 units of the drug, while the syringe 310 in FIG. 5B has a "2" printed near one end of the barrel 320 and 2 rings printed near the opposite end of the barrel 320 and thus contains a concentration of 2 mL of diluent per 100 units of the drug.

In another such implementation, an "A" syringe (marked "A" and/or having one ring around the barrel) may indicate that the drug in the syringe has been reconstituted or diluted at a concentration of 1.0 mL of saline for every 100 units of the drug, a "B" syringe (marked "B" and/or having two rings around the barrel) may indicate that the drug in the syringe has been reconstituted or diluted at a concentration of 2.0 mL of saline for every 100 units of the drug, a "C" syringe (marked "C" and/or having three rings around the barrel) may indicate that the drug in the syringe has been reconstituted or diluted at a concentration of 2.5 mL of saline for every 100 units of the drug, a "D" syringe (marked "D" and/or having four rings around the barrel) may indicate that the drug in the syringe has been reconstituted or diluted at a concentration of 4.0 mL of saline for every 100 units of the drug, and an "E" syringe (marked "E" and/or having five rings around the barrel) may indicate that the drug in the syringe has been reconstituted or diluted at a concentration of 8.0 mL of saline for every 100 units of the drug. In this example, it will be appreciated that a 1 mL "A" syringe, if fully drawn up, would thus contain 100 units of the drug, a 1 mL "B" syringe, if fully drawn up, would thus contain 50 units of the drug, a 1 mL "C" syringe, if fully drawn up, would thus contain 40 units of the drug, a 1 mL "D" syringe, if fully drawn up, would thus contain 25 units of the drug, and a 1 mL "E" syringe, if fully drawn up, would thus contain 12.5 units of the drug.

Alternatively, the markings (number 42, rings 44, or the like) may be used to more directly indicate the number of units contained in the syringe 10,110,210,310.

Color-coding may also be utilized on one or more parts of the syringe 10,110,210,310 to make it easier to distinguish, both for those reconstituting the drug and for those drawing up the syringe 10,110,210,310, the number of units that are or should be contained therein. For example, all or portions of the barrel 20,120,220,320, the plunger handle 36, and/or the cap over the needle 18 may be made of colored material or otherwise colored in some way based on the capacity of the syringe 10,110,210,310, the number of units contained therein, or the like. The colors may likewise be coordinated with printed material included on charts, instructions, packaging, or the like in order to established a uniform, easily-followed guide for reconstitution and use of the drug and the syringe 10,110,210,310.

In one such implementation, a "#1" syringe includes a red plunger handle and needle cap, a "#2" syringe includes an orange plunger handle and needle cap, a "#3" syringe includes a yellow plunger handle and needle cap, a "#4" syringe includes a green plunger handle and needle cap, a "#5" syringe includes a blue plunger handle and needle cap, and accompanying packaging and printed instructions include color-coordination information and indicia to help the user utilize each syringe properly such that the concentrations described previously for #1, #2, #3, #4 and #5 syringes are drawn up in each one.

Information about the chosen color coding system may also be disseminated to patients so that they may readily recognize, understand and use the proper concentration, and thus the proper number of units of the drug.

In at least one embodiment, the barrel 20,120,220,320, the plunger handle 36, and the cap are marked with the generic name and/or the brand name of the drug in order to assure that the syringe 10,110,210,310 is assembled properly and used with the proper drug.

The dimensions of the syringe 10,110,210,310 are chosen so that a sufficient volume of injectable fluid may be drawn up within the interior cylinder 22 for administration to a patient. The barrel 20,120,220,320 of the syringe 10,110,210,310 may be constructed of any conventional syringe material, including glass, polyethylene, polycarbonate, or polyvinyl or other synthetic polymer or various other plastics, and is preferably transparent or translucent such that the fluid or plunger assembly 30 may be viewed within. The plunger assembly 30 is likewise constructed from any suitable inert material including, but not limited to, plastic, vinyl, polyethylene, rubber, platinum-cured silicon or TEFLON®. In at least one embodiment, the interior volume of the syringe 10,110,210, 310 is slightly more than 1 mL such that an amount of substantially exactly 1 mL of injectable fluid may be contained therein. However, it will be appreciated that other volumes may likewise be utilized.

Figure 6:
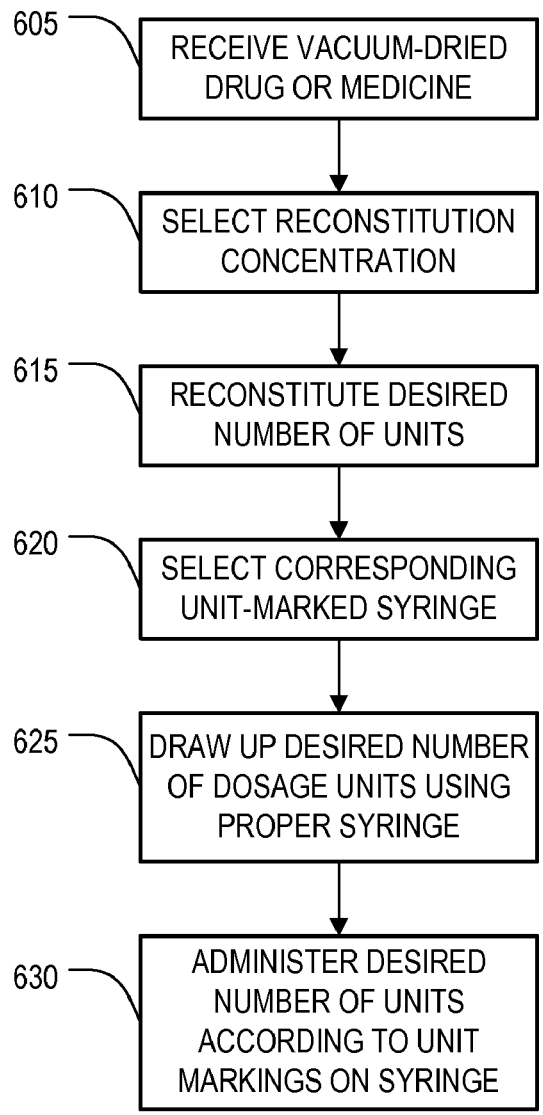
FIG. 6 is a flowchart illustrating the steps of a method of use in accordance with one or more preferred embodiments of the present invention.

FIG. 6 is a flowchart illustrating the steps of a method of use 600 in accordance with one or more preferred embodiments of the present invention. The method 600 begins at step 605 with the receipt, by a medical practitioner, facility, organization of the like of an injectable drug, medicine or the like in dry, reconstitutable form. Such injectable drugs or medicines are often provided in vacuum-dried form, and include, without limitation, botulinum toxin type A (sold or planning to be sold under the trade names BOTOX®, Dysport®, Reloxin™ and Puretox™) and botulinum toxin type B (sold under the trade name Myobloc®), both frequently administered for the treatment of facial wrinkles Botox, for example, is typically supplied in vials containing 100 units of Botox in dry form.

Such dry-form drugs may often be reconstituted in a variety of concentrations, often depending on practitioner preference. For example, Botox is commonly reconstituted in concentrations of 1.0 mL of diluent (typically nonpreserved normal saline, or 0.9% sodium chloride injection) per 100 units of Botox for a dosage concentration of 10.0 U of Botox per 0.1 mL (100 U/1 mL), 2.0 mL of diluent per 100 units of Botox for a dosage concentration of 5.0 U of Botox per 0.1 mL (50 U/1.0 mL), 2.5 mL of diluent per 100 units of Botox for a dosage concentration of 4.0 U of Botox per 0.1 mL (40 U/1 mL), 4.0 mL of diluent per 100 units of Botox for a dosage concentration of 2.5 U of Botox per 0.1 mL (25 U/1 mL), or 8.0 mL of diluent per 100 units of Botox for a dosage concentration of 1.25 U of Botox per 0.1 mL (12.5 U/1 mL). At step 510, a desired reconstitution concentration is selected. Preferably, the concentration is selected according to a particular policy, e.g., a particular medical facility may have a policy of providing all dosages in a concentration of 50 U/1 mL, or according to a particular prescription, e.g., a practitioner may prescribe use of a concentration of 40 U/1 mL.

At step 615, a desired number of units may be reconstituted according to the desired dosage concentration. Perhaps most conveniently, an entire vial of the vacuum-dried drug may be reconstituted at once, but portions of vials may in some cases be reconstituted, or multiple vials are reconstituted at once. Reconstitution may be carried out according to conventional procedures, and care should be taken to ensure that the proper concentration is achieved and properly labeled or otherwise tracked before being drawn up into individual syringes.

Based on the dosage concentration present in the injectable fluid, one or more corresponding syringe is selected at step 620 for use therewith. More particularly, a syringe, such as the hypodermic syringe 10 of FIG. 2, having unit markings corresponding with the dosage concentration is selected for use with the dosage concentration. Care should be taken to ensure that only a properly-marked syringe is utilized for each particular dosage concentration. The syringe 10 in FIG. 2, for example, is labeled for use with a dosage concentration of 50 U/1 mL, and thus should only be used for an injectable fluid having a dosage concentration of 50 U/1 mL. On the other hand, the syringe 110 in FIG. 4 is labeled for use with a dosage concentration of 40 U/1 mL, and thus should only be used for an injectable fluid having a dosage concentration of 40 U/1 mL.

Figure 7:
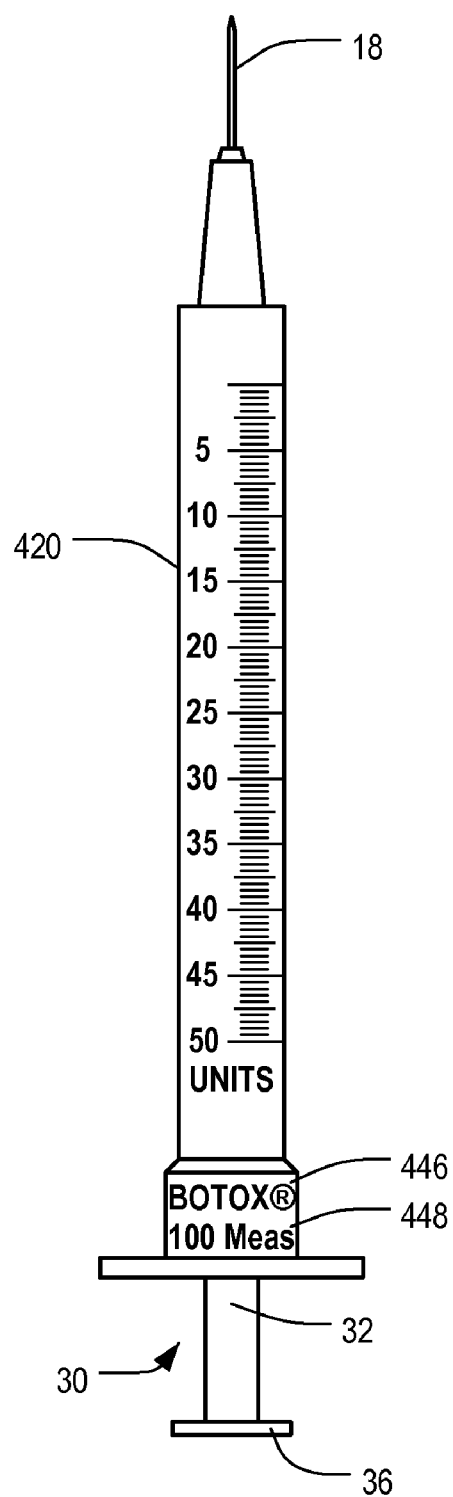
FIG. 7 is a side view of a hypodermic syringe similar to that of FIG. 2 but marked with a manufacturing source identifier and an indication of the unit measure.

It is also recognized that different drugs are provided by different manufacturers in different standard units. For example, although Botox and Dysport are very similar, Botox is commonly provided by the manufacturer in 100-unit packages or increments, while Dysport is commonly provided by the manufacturer in 300-unit packages or increments, and the relative units are not necessarily equivalent. Thus, to help ensure that reconstituted units of a drug are drawn up or otherwise utilized with a syringe that is properly calibrated for that drug, each syringe may be marked with an indication of the drug manufacturer with which the syringe is to be used, with an indication of the standard number of units in which the drug is to be used, or both. For example, FIG. 7 is a side view of a hypodermic syringe 410 similar to that of FIG. 2 but marked with a manufacturing source identifier 446 and an indication 448 of the unit measure. In particular, the manufacturing source identifier 446 on the syringe 410 in FIG. 7 indicates that the syringe 410 is to be used with BOTOX®, which is manufactured by (or possibly under license from) Allergan, Inc. of Irvine, Calif., and the unit measure indication 448 on the syringe 410 in FIG. 7 indicates that the syringe 410 is to be used with a drug, such as BOTOX®, that is supplied in 100-unit increments (rather than, for example, a drug, such as DYSPORT®, that is supplied in 300-unit increments. Selection of a syringe based on manufacturing source identifier 446, unit measure indication 448, or both may be incorporated into step 620.

Figure 8:
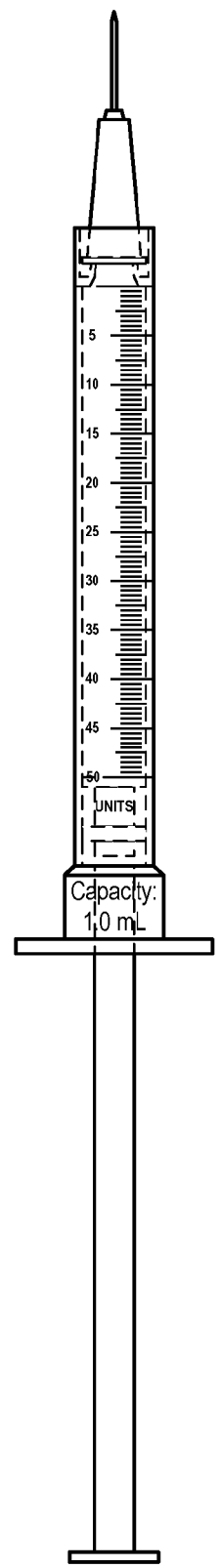
FIG. 8 is a side view of the hypodermic syringe of FIG. 2, shown with a full 50 units drawn up therein.

Using the proper syringe 10,110,210,310,410 an amount of the injectable fluid corresponding to a desired number of units of the drug may be drawn up at step 625. For example, FIG. 8 is a side view of the hypodermic syringe 10 of FIG. 2, shown with a full 50 units drawn up therein. Finally, a desired number of units (which may be some or all of the units that have been drawn up) are administered at each injection site at step 630.

Advantageously, assuming the proper concentration is prepared, the syringes and methods of use of the present invention help to ensure that each syringe is drawn up with the proper concentration of drug. Also advantageously, assuming the proper concentration is prepared and properly drawn into the syringe, the syringes and methods of use of the present invention help to ensure that the proper dosage of the drug is injected. Also advantageously, assuming the proper concentration is prepared and properly drawn into the syringe, the syringes and methods of use of the present invention help to ensure that the patient receives the proper number of units of the drug. Overall, although the present invention cannot prevent an individual from intentionally preparing the wrong concentration or utilizing the wrong syringe for the reconstituted drug, the syringes and methods of use of the present invention advantageously help to avoid accidental errors of these types.

Based on the foregoing information, it is readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention.

Accordingly, while the present invention has been described herein in detail in relation to its preferred embodiment, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements; the present invention being limited only by the claims appended hereto and the equivalents thereof. Although specific terms are employed herein, they are used in a generic and descriptive sense only and not for the purpose of limitation.

What is claimed is:

1. A method of reconstituting and administering an injectable drug or medicine, distributed to practitioners in dry form, comprising:
   receiving a drug or medicine in dry form;
   selecting a reconstitution concentration for the drug or medicine;
   reconstituting a desired number of units of the drug or medicine by adding diluent to the dry-form drug or medicine;
   selecting a syringe that is pre-marked in correspondence to the selected reconstitution concentration;
   after selecting the pre-marked syringe, drawing up a desired number of drug or medicine units using the selected syringe; and
   administering a desired number of units according to the unit markings on the selected syringe.

2. The method of claim 1, wherein the step of selecting a reconstitution concentration includes selecting the reconstitution concentration from a plurality of different standardized reconstitution concentrations.

3. The method of claim 2, wherein the step of selecting a syringe includes selecting the syringe from a plurality of differently-marked syringes, wherein the markings on each of the plurality of syringes is representative of a particular standardized reconstitution concentration of the plurality of different standardized reconstitution concentrations.

4. The method of claim 3, wherein the selected syringe is pre-marked with dosage units according to the selected reconstitution concentration, thereby directly indicating to a user the number of dosage units of the drug contained in the syringe.

5. The method of claim 3, wherein the selected syringe is marked with an alphanumeric character indicating, to a user, the selected reconstitution concentration.

6. The method of claim 5, wherein the alphanumeric character includes a number representative of the number of mL of diluent to be added to a predetermined quantity of the dry-form drug, thereby reconstituting the drug.

7. The method of claim 6, wherein the predetermined quantity of the dry-form drug is 100 units.

8. The method of claim 6, wherein the predetermined quantity of the dry-form drug is 300 units.

9. The method of claim 5, wherein the alphanumeric character includes a letter.

10. The method of claim 5, wherein the alphanumeric character includes a code representative of the selected reconstitution concentration.

11. The method of claim 3, wherein the selected syringe is marked with a non-alphanumeric code that is representative of the selected reconstitution concentration.

12. The method of claim 11, wherein the non-alphanumeric code includes one or more rings wherein the number of rings is indicative of the selected reconstitution concentration.

13. The method of claim 11, wherein the non-alphanumeric code includes a color code wherein the color of one or more elements of the syringe are indicative of the selected reconstitution concentration.

14. The method of claim 3, wherein the reconstituting step includes reconstituting the desired number of units of the drug or medicine by adding the diluent to the dry-form drug or medicine at the selected reconstitution concentration.

15. The method of claim 3, wherein the selected syringe is marked with a manufacturing source identifier, thereby indirectly providing an indication of the unit measure, of a plurality of possible unit measures, with which the selected syringe is to be used.

16. The method of claim 3, wherein the selected syringe is marked with an indication of the unit measure, of a plurality of possible unit measures, with which the selected syringe is to be used.

17. A method of distributing an injectable drug or medicine, provided in dry form, for reconstitution and administration, comprising:

packaging an injectable drug or medicine, in dry form, for distribution;

procuring a supply of syringes for use with a reconstituted form of the dry-form injectable drug or medicine, wherein each syringe is marked in such a way as to indicate, to a user, the concentration of the drug or medicine to be contained in the syringe when reconstituted and drawn thereinto, and wherein the supply of syringes include a multitude of each of a plurality of differently-marked syringes such that different syringes are to be used with different reconstitution concentrations; and providing a quantity of the injectable drug or medicine to a practitioner in conjunction with one or more syringe together with printed information instructing a user with regard to the reconstitution of the drug or medicine in the concentration corresponding to the marking on the one or more syringe.

\* \* \* \* \*